(12) United States Patent
Lee et al.

(10) Patent No.: US 7,037,927 B2
(45) Date of Patent: May 2, 2006

(54) AMIDES THAT INHIBIT VANILLOID RECEPTOR SUBTYPE 1 (VR1) RECEPTOR

(75) Inventors: Chih-Hung Lee, Vernon Hills, IL (US); John R. Koenig, Chicago, IL (US); Brian S. Brown, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 172 days.

(21) Appl. No.: 10/687,164

(22) Filed: Oct. 16, 2003

(65) Prior Publication Data

US 2005/0085512 A1  Apr. 21, 2005

(51) Int. Cl.
C07D 213/02 (2006.01)
A61K 31/44 (2006.01)

(52) U.S. Cl. ............ 514/344; 514/256; 514/357; 514/365; 514/374; 514/378; 514/406; 514/438; 544/335; 546/286; 546/336; 548/145; 548/215; 548/240; 548/273.1; 549/29

(58) Field of Classification Search ......... 514/357, 514/617, 344, 365, 374, 378, 406, 438, 256; 546/336, 286; 564/161; 544/335; 548/146, 548/215, 240, 273.1; 549/29
See application file for complete search history.

(56) References Cited

U.S. PATENT DOCUMENTS 6,462,036 B1 * 10/2002 Doyle et al. ............... 514/218

FOREIGN PATENT DOCUMENTS

| EP | 533267 | * | 9/1992 |
| EP | 0 513 379 A1 | | 11/1992 |
| EP | 0 533 267 A1 | | 3/1993 |
| EP | 896821 | * | 2/1999 |
| JP | 2001-139550 | * | 5/2001 |
| WO | 90/09989 | | 9/1990 |
| WO | 93/16053 | | 8/1993 |
| WO | 95/04729 | | 2/1995 |
| WO | 00/06085 | | 2/2000 |
| WO | WO 00/46203 | * | 8/2000 |
| WO | WO 00/78726 A1 | * | 12/2000 |
| WO | 02/10146 | | 2/2002 |
| WO | 03/003008 | | 1/2003 |
| WO | WO 03/027081 | * | 4/2003 |
| WO | 2004/009563 | | 1/2004 |
| WO | 2004/056347 | | 7/2004 |
| WO | 2004/056774 | | 7/2004 |

OTHER PUBLICATIONS

Basha et al, J. Chem. Soc., Chem. Commun., vol. 4, pp. 305-306, 1987.*
Fujisawa Pharmaceutical Co., Ltd, CA 132: 49960, 1999 of JP 11349572.*
Abromovitch et al., "Arylpyridines, Part I. Orientation in the reaction of phenyllithium with some 3-substituted pyridines," Can. J. Chem. 38:761-771 (1960).
Caterina et al., "Impaired nociception and pain sensation in mice lacking the capsaicin receptor," Science 288:306-313 (2000).
Caterina et al., "The capsaicin receptor: a heat-activated ion channel in the pain pathway," Nature 289:816-824 (1997).
Caterina et al., "The vanilloid receptor: a molecular gateway to the pain pathway," Annu. Rev. Neurosci. 24:487-517 (2001).
Collier et al., "The abdominal constriction response and its suppression by analgesic drugs in the mouse," Br. J. Pharmac. Chemother. 32:295-310 (1968).
Davis et al., "Vanilloid receptor-1 is essential for inflammatory thermal hyperalgesia," Nature 405:183-187 (2000).
Fowler, "Intravesical treatment of overactive bladder," Urology 55(Supp. 5A):60-64 (2000).
Hayes et al., "Cloning and functional expression of a human orthologue of rat vanilloid receptor-1," Pain 88:205-215 (2000).
Jones, "The synthesis of some amines and amino acids containing the pyrazole nucleus," J. Am. Chem. Soc. 71:3994-4000 (1949).

(Continued)

Primary Examiner—Zinna Northington Davis
(74) Attorney, Agent, or Firm—Gabryleda Ferrari-Dileo

(57) ABSTRACT

The present invention relates to compounds of formula (I)

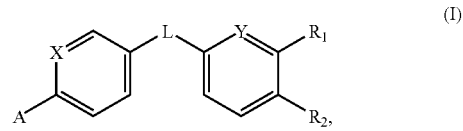

that are novel VR1 antagonists useful in treating pain, inflammatory thermal hyperalgesia, urinary incontinence, or bladder overactivity.

7 Claims, No Drawings

OTHER PUBLICATIONS

Loew, Chem. Ber. 23:1452 (1890).

Nolano et al., "Topical capsaicin in humans: parallel loss of epidermal nerve fibers and pain sensation," Pain 81:135-145 (1999).

Bachmann, W.E. & Barton, S.M.X., "The Relative Proportions of Stereoisomeric Oximes Formed in the Oximation of Unsysmmetrical Ketones", *Journ of Organic Chem.*, 3:300-311 (1938).

Beer, P.D., et al., "New Classes of Anion Receptor containing Charged and Neutral Transition Metal Lewis Acidic Recognition Sites", *Journ of the Chem Soc, Chem. Comm.*, 10:828-830 (1993).

Cain, B.F., et al., "Potential Antitumor Agents. Ix. Bisquaternary Salts", *Journ of Medic Chem.*, 11(5):963-966 (1968).

Eric, B., et al., "Über eineSynthese von Pyridin-ketonen . . . " *Berichte der Deutschen Chemischen Gesellschaft*, 57:828-834 (1924).

Hales, N.J. & Beattie, J.F., "Novel Inhibitors of Prolyl 4-Hydroxylase. T. The Intriguing Structure-Activity Relationships Seen with 2,2'-Bipyridine and its 5,5'-Dicarboxylic Acid Derivatives", *J Med Chem.*, 36:3853-3858 (1992).

Accession No.: 2142678, Dataase Crossfire Beilstein Beilstein Institut Zur Foederung Der Chemischen Wissenschaften, Frankfurt AM Main.

* cited by examiner

AMIDES THAT INHIBIT VANILLOID RECEPTOR SUBTYPE 1 (VR1) RECEPTOR

TECHNICAL BACKGROUND

The present invention relates to compounds of formula (I), which are useful for treating disorders caused by or exacerbated by vanilloid receptor activity and pharmaceutical compositions containing compounds of formula (I) which are useful in treating pain, bladder overactivity, and urinary incontinence.

BACKGROUND OF INVENTION

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as VR1. The intradermal administration of capsaicin is characterized by an initial burning or hot sensation followed by a prolonged period of analgesia. The analgesic component of VR1 receptor activation is thought to be mediated by a capsaicin-induced desensitization of the primary sensory afferent terminal. Thus, the long lasting anti-nociceptive effects of capsaicin has prompted the clinical use of capsaicin analogs as analgesic agents. Further, capsazepine, a capsaicin receptor antagonist can reduce inflammation-induced hyperalgesia in animal models. VR1 receptors are also localized on sensory afferents which innervate the bladder. Capsaicin or resiniferatoxin has been shown to ameliorate incontinence symptoms upon injection into the bladder.

The VR1 receptor has been called a "polymodal detector" of noxious stimuli since it can be activated in several ways. The receptor channel is activated by capsaicin and other vanilloids and thus is classified as a ligand-gated ion channel. VR1 receptor activation by capsaicin can be blocked by the competitive VR1 receptor antagonist, capsazepine. The channel can also be activated by protons. Under mildly acidic conditions (pH 6–7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Electrophysiological studies of sensory neurons (dorsal root ganglia) from mice lacking the VR1 receptor revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The VR1 (−/−) mice also did not show reduced sensitivity to nerve injury-induced mechanical or thermal nociception. However, the VR1 knock-out mice were insensitive to the noxious effects of intradermal capsaicin, exposure to intense heat (50–55° C.), and failed to develop thermal hyperalgesia following the intradermal administration of carrageenan.

The compounds of the present invention are novel VR1 antagonists and have utility in treating pain, bladder overactivity, and urinary incontinence.

SUMMARY OF THE PRESENT INVENTION

The present invention discloses novel amides, a method for inhibiting the VR1 receptor in mammals using these amides, a method for controlling pain in mammals, and pharmaceutical compositions including those amides. More particularly, the present invention is directed to compounds of formula (I)

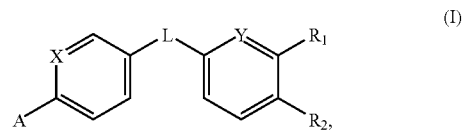

or a pharmaceutically acceptable salt, amide, ester, or prodrug thereof, wherein
  A is aryl or heteroaryl;
  X is CH or N;
  Y is CH or N;
  L is —C(O)N($R_3$)— or —N($R_3$)C(O)—;
  $R_1$ and $R_2$ are independently hydrogen, alkoxy, alkyl, aryloxy, haloalkoxy, haloalkyl, halogen, or heterocycle; and
  $R_3$ is hydrogen or alkyl.

DETAILED DESCRIPTION OF THE PRESENT INVENTION

In the principle embodiment, compounds of formula (I) are disclosed

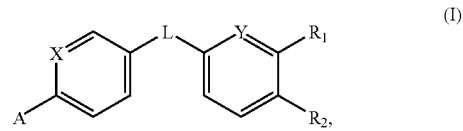

or a pharmaceutically acceptable salt, amide, ester, or prodrug thereof, wherein
  A is aryl or heteroaryl;
  X is CH or N;
  Y is CH or N;
  L is —C(O)N($R_3$)— or —N($R_3$)C(O)—;
  $R_1$ and $R_2$ are independently hydrogen, alkoxy, alkyl, aryloxy, haloalkoxy, haloalkyl, halogen, or heterocycle; and
  $R_3$ is hydrogen or alkyl.

In another embodiment, the present invention relates to a compound of formula (I) wherein A is heteroaryl; X is CH or N; Y is CH or N; L is —C(O)N($R_3$)—; and $R_1$, $R_2$, and $R_3$ are as defined in formula (I).

In another embodiment, the present invention relates to a compound of formula (I) wherein A is heteroaryl; X is CH; Y is CH; L is —C(O)N($R_3$)—; and $R_1$ and $R_2$ are independently hydrogen, alkoxy, alkyl, haloalkoxy, or haloalkyl; and $R_3$ is as defined in formula (I).

In another embodiment, the present invention relates to a compound of formula (I) wherein A is heteroaryl wherein the heteroaryl is 2-pyridinyl optionally substituted with 1 substituent selected from cyano, halogen, nitro, or —$NR_AR_B$; $R_A$ and $R_B$ are independently hydrogen, alkoxycarbonyl, alkylcarbonyl, alkylsulfonyl, or haloalkylsulfonyl; X is CH; Y is CH; L is —$C(O)N(R_3)$—; $R_1$ and $R_2$ are independently hydrogen, alkoxy, alkyl, haloalkoxy, or haloalkyl; and $R_3$ is hydrogen.

In another embodiment, the present invention relates to a compound of formula (I) wherein A is heteroaryl wherein the heteroaryl is 2-pyridinyl optionally substituted with 1 substituent selected from cyano, halogen, nitro, —$NR_AR_B$, or ($NR_CR_D$)sulfonyl; $R_A$ and $R_B$ are independently hydrogen, alkoxycarbonyl, alkylcarbonyl, alkylsulfonyl, or haloalkylsulfonyl; $R_C$ and $R_D$ are independently hydrogen or alkyl; X is CH; Y is CH; L is —$C(O)N(R_3)$—; $R_1$ is hydrogen; $R_2$ is alkoxy, alkyl, haloalkoxy, or haloalkyl; and $R_3$ is hydrogen.

In another embodiment, the present invention relates to a compound of formula (I) wherein A is heteroaryl wherein the heteroaryl is 3-[(dimethylamino)sulfonyl]-2-pyridinyl; X is CH; Y is CH; L is —$C(O)N(R_3)$—; $R_1$ and $R_3$ are hydrogen; and $R_2$ is alkyl wherein a preferred alkyl group is tert-butyl.

In another embodiment, the present invention relates to a compound of formula (I) wherein A is heteroaryl wherein the heteroaryl is imidazolyl, isoxazolyl, oxazolyl, pyrazolyl, pyrimidinyl, tetraazolyl, thiazolyl, or thienyl, wherein the heteroaryl is optionally substituted with 1 substituent selected from alkylsulfonyl, halogen, or haloalkyl; X is CH; Y is CH; L is —$C(O)N(R_3)$—; $R_1$ and $R_2$ are independently hydrogen, alkoxy, alkyl, haloalkoxy, or haloalkyl; and $R_3$ is hydrogen.

In another embodiment, the present invention relates to a compound of formula (I) wherein A is heteroaryl wherein the heteroaryl is imidazolyl, isoxazolyl, oxazolyl, pyrazolyl, pyrimidinyl, tetraazolyl, thiazolyl, or thienyl, wherein the heteroaryl is optionally substituted with 1 substituent selected from alkylsulfonyl, halogen, or haloalkyl; X is CH; Y is CH; L is —$C(O)N(R_3)$—; $R_1$ is hydrogen; $R_2$ is alkoxy, alkyl, haloalkoxy, or haloalkyl; and $R_3$ is hydrogen.

In another embodiment, the present invention relates to a compound of formula (I) wherein A is heteroaryl; X is CH; Y is CH; L is —$C(O)N(R_3)$—; $R_1$ is hydrogen, alkoxy, alkyl, haloalkoxy, haloalkyl, or halogen; $R_2$ is heterocycle; and $R_3$ is as defined in formula (I).

In another embodiment, the present invention relates to a compound of formula (I) wherein A is heteroaryl wherein the heteroaryl is pyridinyl or pyrazolyl, wherein the heteroaryl is optionally substituted with 1 substituent selected from alkylsulfonyl, halogen, or haloalkyl; X is CH; Y is CH; L is —$C(O)N(R_3)$—; $R_1$ is hydrogen or halogen; $R_2$ is heterocycle wherein the heterocycle is azepanyl, piperidinyl, or pyrrolidinyl; and $R_3$ is hydrogen.

In another embodiment, the present invention relates to a compound of formula (I) wherein A is heteroaryl wherein the heteroaryl is 3-[(dimethylamino)sulfonyl]-2-pyridinyl; X is CH; Y is CH; L is —$C(O)N(R_3)$—; $R_1$ is hydrogen; $R_2$ is heterocycle wherein the heterocycle is azepanyl, piperidinyl, or pyrrolidinyl; and $R_3$ is hydrogen.

In another embodiment, the present invention relates to a compound of formula (I) wherein A is heteroaryl; X is CH or N; Y is CH or N; L is —$C(O)N(R_3)$—; $R_1$ is hydrogen, alkoxy, alkyl, haloalkoxy, haloalkyl, or halogen; $R_2$ is aryloxy; and $R_3$ is as defined in formula (I).

In another embodiment, the present invention relates to a compound of formula (I) wherein A is heteroaryl; X is CH; Y is CH; L is —$C(O)N(R_3)$—; $R_1$ is hydrogen, alkoxy, alkyl, haloalkoxy, haloalkyl, or halogen; $R_2$ is aryloxy; and $R_3$ is as defined in formula (I).

In another embodiment, the present invention relates to a compound of formula (I) wherein A is heteroaryl wherein the heteroaryl is 2-pyridinyl optionally substituted with 1 substituent selected from cyano, halogen, nitro, —$NR_AR_B$, or ($NR_CR_D$)sulfonyl; $R_A$ and $R_B$ are independently hydrogen, alkoxycarbonyl, alkylcarbonyl, alkylsulfonyl, or haloalkylsulfonyl; $R_C$ and $R_D$ are independently hydrogen or alkyl; X is CH; Y is CH; L is —$C(O)N(R_3)$—; $R_1$ is hydrogen, alkoxy, alkyl, haloalkoxy, haloalkyl, or halogen; $R_2$ is aryloxy; and $R_3$ is as defined in formula (I).

In another embodiment, the present invention relates to a compound of formula (I) wherein A is heteroaryl wherein the heteroaryl is 2-pyridinyl optionally substituted with 1 substituent selected from halogen; X is CH; Y is CH; L is —$C(O)N(R_3)$—; $R_1$ is hydrogen; $R_2$ is aryloxy wherein the aryl of aryloxy is phenyl; and $R_3$ is hydrogen.

In another embodiment, the present invention relates to a compound of formula (I) wherein A is aryl; X is CH or N; Y is CH or N; L is —$C(O)N(R_3)$—; and $R_1$, $R_2$, and $R_3$ are as defined in formula (I).

In another embodiment, the present invention relates to a compound of formula (I) wherein A is aryl; X is N; Y is CH; L is —$C(O)N(R_3)$—; $R_1$ and $R_2$ are independently hydrogen, alkoxy, alkyl, haloalkoxy, or haloalkyl; and $R_3$ is as defined in formula (I).

In another embodiment, the present invention relates to a compound of formula (I) wherein A is aryl wherein the aryl is phenyl; X is N; Y is CH; L is —$C(O)N(R_3)$—; $R_1$ is hydrogen; $R_2$ is alkyl wherein a preferred alkyl is tert-butyl; and $R_3$ is hydrogen.

In another embodiment, the present invention relates to a compound of formula (I) wherein A is heteroaryl; X is CH or N; Y is CH or N; L is —$N(R_3)C(O)$—; and $R_1$, $R_2$, and $R_3$ are as defined in formula (I).

In another embodiment, the present invention relates to a compound of formula (I) wherein A is heteroaryl; X is CH; Y is CH; L is —$N(R_3)C(O)$—; $R_1$ and $R_2$ are independently hydrogen, alkoxy, alkyl, haloalkoxy, or haloalkyl; and $R_3$ is as defined in formula (I).

In another embodiment, the present invention relates to a compound of formula (I) wherein A is heteroaryl wherein the heteroaryl is 2-pyridinyl optionally substituted with cyano, halogen, nitro, —$NR_AR_B$, or ($NR_CR_D$)sulfonyl; $R_A$ and $R_B$ are independently hydrogen, alkoxycarbonyl, alkylcarbonyl, alkylsulfonyl, or haloalkylsulfonyl; $R_C$ and $R_D$ are independently hydrogen or alkyl; X is CH; Y is CH; L is —$N(R_3)C(O)$—; $R_1$ is hydrogen; $R_2$ is alkoxy, alkyl, haloalkoxy, or haloalkyl; and $R_3$ is as defined in formula (I).

In another embodiment, the present invention relates to a compound of formula (I) wherein A is heteroaryl wherein the heteroaryl is 2-pyridinyl optionally substituted with halogen; X is CH; Y is CH; L is —$N(R_3)C(O)$—; $R_1$ is hydrogen; $R_2$ is alkyl wherein a preferred alkyl is tert-butyl; and $R_3$ is hydrogen.

Another embodiment of the present invention relates to pharmaceutical compositions comprising a therapeutically effective amount of a compound of formula (I) or a pharmaceutically acceptable salt thereof.

Another embodiment of the present invention relates to a method of treating a disorder wherein the disorder is ameliorated by inhibiting vanilloid receptor subtype 1 (VR1) receptor in a mammal, comprising administering a therapeutically effective amount of a compound of formula (I) or a pharmaceutically acceptable salt thereof.

Another embodiment of the present invention relates to a method for treating pain in a mammal, comprising administering a therapeutically effective amount of a compound of formula (I) or a pharmaceutically acceptable salt thereof.

Another embodiment of the present invention relates to a method of treating urinary incontinence in a mammal, comprising administering a therapeutically effective amount of a compound of formula (I) or a pharmaceutically acceptable salt thereof.

Another embodiment of the present invention relates to a method of treating bladder overactivity in a mammal, comprising administering a therapeutically effective amount of a compound of formula (I) or a pharmaceutically acceptable salt thereof.

Another embodiment of the present invention relates to a method of treating inflammatory thermal hyperalgesia in a mammal, comprising administering a therapeutically effective amount of a compound of formula (I) or a pharmaceutically acceptable salt thereof.

Definition of Terms

As used throughout this specification and the appended claims, the following terms have the following meanings:

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a monocyclic-ring system, a bicyclic-fused ring system, or a tricyclic-fused ring system wherein one or more of the fused rings are aromatic. Representative examples of aryl include, but are not limited to, anthracenyl, azulenyl, fluorenyl, 2,3-dihydroindenyl, indenyl, naphthyl, phenyl, and tetrahydronaphthyl.

The aryl groups of this invention can be substituted with 1, 2, or 3 substituents independently selected from alkenyl, alkoxy, alkoxyalkyl, alkoxycarbonyl, alkoxycarbonylalkyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halogen, hydroxy, hydroxyalkyl, mercapto, nitro, —$NR_AR_B$, ($NR_CR_D$)carbonyl, and ($NR_CR_D$)sulfonyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "carbonyl" as used herein, means a —C(O)— group.

The term "carboxy" as used herein, means a —$CO_2H$ group.

The term "cyano" as used herein, means a —CN group.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, refers to an aromatic five- or six-membered ring wherein 1, 2, 3, or 4 heteroatoms are independently selected from N, O, or S. The five membered rings have two double bonds and the six membered rings have three double bonds. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetraazolyl, thiadiazolyl, thiazolyl, thienyl, triazolyl, and triazinyl.

The heteroaryl groups of the present invention are optionally substituted 1, 2, 3, or 4 substituents independently selected from alkenyl, alkoxy, alkoxyalkyl, alkoxycarbonyl, alkoxycarbonylalkyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halogen, hydroxy, hydroxyalkyl, mercapto, nitro, —$NR_AR_B$, $(NR_CR_D)$carbonyl, and $(NR_CR_D)$sulfonyl. Representative examples include, but are not limited to, 3-acetylamino-2-pyridinyl, 3-acetyl(methylsulfonyl)amino-2-pyridinyl, 3-amino-2-pyridinyl, 3-bis(methylsulfonyl)amino-2-pyridinyl, 3-bis(chloromethylsulfonyl)amino-2-pyridinyl, 3-bromo-2-pyridinyl, 6-bromo-2-pyridinyl, 3-chloro-2-pyridinyl, 3-cyano-2-pyridinyl, 3-nitro-2-pyridinyl, 3-(methoxycarbonyl)amino-2-pyridinyl, 3-fluoro-2-pyridinyl, 1-(methylsulfonyl)-1H-imidazol-2-yl, and 5-(trifluoromethyl)-1H-pyrazol-1-yl.

The term "heterocycle," as used herein, refers to a three, four, five, six, seven or eight membered ring containing one or two heteroatoms independently selected from the group consisting of nitrogen, oxygen, and sulfur. The three membered ring has zero double bonds. The four and five membered ring has zero or one double bond. The six membered ring has zero, one, or two double bonds. The seven and eight membered rings have zero, one, two, or three double bonds. The heterocycle groups of the present invention can be attached to the parent molecular moiety through a carbon atom or a nitrogen atom. Representative examples of heterocycle include, but are not limited to, azetidinyl, azepanyl, aziridinyl, azocanyl, morpholinyl, piperazinyl, piperidinyl, pyrrolidinyl, and thiomorpholinyl.

The heterocycles of the present invention are optionally substituted with 1, 2, 3, or 4 substituents independently selected from alkenyl, alkoxy, alkoxyalkyl, alkoxycarbonyl, alkoxycarbonylalkyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halogen, hydroxy, hydroxyalkyl, mercapto, nitro, —$NR_AR_B$, $(NR_CR_D)$carbonyl, and $(NR_CR_D)$sulfonyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "—$NR_AR_B$" as used herein, means two groups, $R_A$ and $R_B$, which are appended to the parent molecular moiety through a nitrogen atom. $R_A$ and $R_B$ are each independently hydrogen, alkoxycarbonyl, alkyl, alkylcarbonyl, alkylsulfonyl, formyl, or haloalkylsulfonyl. Representative examples of —$NR_AR_B$ include, but are not limited to, amino, methylamino, acetylamino, acetylmethylamino, (acetyl)(methylsulfonyl)amino, (methylsulfonyl)amino, bis(methylsulfonyl)amino, (chloromethylsulfonyl)amino, bis(chloromethylsulfonyl)amino, and (methoxycarbonyl)amino.

The term "—$NR_CR_D$" as used herein, means two groups, $R_C$ and $R_D$, which are appended to the parent molecular moiety through a nitrogen atom. $R_C$ and $R_D$ are each independently hydrogen or alkyl. Representative examples of —$NR_CR_D$ include, but are not limited to, amino, methylamino, dimethylamino, and ethylmethylamino.

The term "$(NR_CR_D)$carbonyl" as used herein, means a —$NR_CR_D$ group, as defined herein, appended to the parent molecular moiety through a carbonyl group, as defined herein. Representative examples of $(NR_CR_D)$carbonyl include, but are not limited to, aminocarbonyl, (methylamino)carbonyl, (dimethylamino)carbonyl, and (ethylmethylamino)carbonyl.

The term "$(NR_CR_D)$sulfonyl" as used herein, means a —$NR_CR_D$ group, as defined herein, appended to the parent molecular moiety through a sulfonyl group, as defined herein. Representative examples of $(NR_CR_D)$sulfonyl include, but are not limited to, aminosulfonyl, (methylamino)sulfonyl, (dimethylamino)sulfonyl, and (ethylmethylamino)sulfonyl.

Compounds of the present invention can exist as stereoisomers, wherein asymmetric or chiral centers are present. Stereoisomers are designated (R) or (S), depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13–30. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution, a technique well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) direct separation of the mixture of optical enantiomers on chiral chromatographic columns, or (3) formation of a diastereomeric salt followed by selective recrystallization of one of the diastereomeric salts.

Compounds of the present invention were named by ACD/ChemSketch version 5.0 (developed by Advanced Chemistry Development, Inc., Toronto, ON, Canada) or were given names consistent with ACD nomenclature.

Preferred compounds of the present invention include:
N-(4-tert-butylphenyl)-4-(2-pyridinyl)benzamide;
N-(4-tert-butylphenyl)-4-(3-nitro-2-pyridinyl)benzamide;
4-(3-amino-2-pyridinyl)-N-(4-tert-butylphenyl)benzamide;
N-(4-tert-butylphenyl)-4-(1H-tetraazol-5-yl)benzamide;
4-[3-(acetylamino)-2-pyridinyl]-N-(4-tert-butylphenyl)benzamide;
N-(4-tert-butylphenyl)-4-(1H-imidazol-2-yl)benzamide;
4-{3-[bis(methylsulfonyl)amino]-2-pyridinyl}-N-(4-tert-butylphenyl)benzamide;
N-(4-tert-butylphenyl)-4-(1,3-thiazol-2-yl)benzamide;
N-(4-tert-butylphenyl)-4-(2-pyrimidinyl)benzamide;
N-[3-fluoro-4-(1-piperidinyl)phenyl]-4-(2-pyridinyl)benzamide;
N-(4-tert-butylphenyl)-4-(3-cyano-2-pyridinyl)benzamide;

N-(4-tert-butylphenyl)-6-phenylnicotinamide;
N-(4-tert-butylphenyl)-4-(2-thienyl)benzamide;
4-{3-[acetyl(methylsulfonyl)amino]-2-pyridinyl}-N-(4-tert-butylphenyl)benzamide;
4-(6-bromo-2-pyridinyl)-N-(4-tert-butylphenyl)benzamide;
methyl 2-(4-{[(4-tert-butylphenyl)amino]carbonyl}phenyl)-3-pyridinylcarbamate;
4-(3-{bis[(chloromethyl)sulfonyl]amino}-2-pyridinyl)-N-(4-tert-butylphenyl)benzamide;
N-(4-tert-butylphenyl)-4-(2-pyridinyl)benzenesulfonamide;
N-(4-tert-butylphenyl)-4-(1H-pyrazol-1-yl)benzamide;
N-(4-tert-butylphenyl)-4-(3-pyridinyl)benzamide;
N-(4-tert-butylphenyl)-6-(1H-pyrazol-1-yl)nicotinamide;
N-(4-tert-butylphenyl)-4-(4-puridinyl)benzamide
N-(4-tert-butylphenyl)-4-(1,3-oxazol-2-yl)benzamide;
N-(4-tert-butylphenyl)-4-(3-chloro-2-pyridinyl)benzamide;
4-(3-chloro-2-pyridinyl)-N-[4-(1-pyrrolidinyl)phenyl]benzamide;
4-(3-chloro-2-pyridinyl)-N-[4-(1-piperidinyl)phenyl]benzamide;
N-[4-(1-azepanyl)phenyl]-4-(3-chloro-2-pyridinyl)benzamide;
4-(3-chloro-2-pyridinyl)-N-(3-methylphenyl)benzamide;
4-(3-chloro-2-pyridinyl)-N-(4-methylphenyl)benzamide;
4-(3-chloro-2-pyridinyl)-N-(4-methoxyphenyl)benzamide;
4-(3-chloro-2-pyridinyl)-N-[3-(trifluoromethoxy)phenyl]benzamide;
4-(3-chloro-2-pyridinyl)-N-(4-phenoxyphenyl)benzamide;
4-(3-chloro-2-pyridinyl)-N-(3,4-dimethylphenyl)benzamide;
4-(3-chloro-2-pyridinyl)-N-(4-ethylphenyl)benzamide;
4-(3-chloro-2-pyridinyl)-N-(4-isopropylphenyl)benzamide;
N-(4-tert-butylphenyl)-4-[1-(methylsulfonyl)-1H-imidazol-2-yl]benzamide;
N-(4-tert-butylphenyl)-4-[5-(trifluoromethyl)-1H-pyrazol-1-yl]benzamide;
N-[4-(1-azepanyl)phenyl]-4-[5-(trifluoromethyl)-1H-pyrazol-1-yl]benzamide;
N-[4-(trifluoromethyl)phenyl]-4-[5-(trifluoromethyl)-1H-pyrazol-1-yl]benzamide;
4-[5-(trifluoromethyl)-1H-pyrazol-1-yl]-N-[5-(trifluoromethyl)-2-pyridinyl]benzamide;
4-tert-butyl-N-[4-(3-chloro-2-pyridinyl)phenyl]benzamide;
N-(4-tert-butylphenyl)-4-(3-isoxazolyl)benzamide;
N-(4-tert-butylphenyl)-4-(3-fluoro-2-pyridinyl)benzamide;
N-(4-tert-butylphenyl)-4-{3-[(dimethylamino)sulfonyl]-2-pyridinyl}benzamide; and
N-[4-(1-azepanyl)phenyl]-4-{3-[(dimethylamino)sulfonyl]-2-pyridinyl}benzamide or pharmaceutically acceptable salts, esters, amides, or prodrugs thereof.

In Vitro Data

Determination of Inhibition Potencies

Dulbecco's modified Eagle medium (D-MEM)(with 4.5 mg/mL glucose) and fetal bovine serum were obtained from Hyclone Laboratories, Inc. (Logan, Utah). Dulbecco's phosphate buffered saline (D-PBS)(with 1 mg/mL glucose and 3.6 mg/l Na pyruvate)(without phenol red), L-glutamine, hygromycin B, and Lipofectamine™ were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxnyl]phenyl]-N-[2-[(acetyloxy)methoxy]-2-oxyethyl]-glycine, 2-(acetyloxy)methyl ester) was purchased from Molecular Probes (Eugene, Oreg.).

The cDNAs for the human VR1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain 88: 205–215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hVR1 cDNA were transfected individually into 1321N1 human astrocytoma cells using Lipofectamine™. Forty-eight hours after transfection, the neomycin-resistant cells were selected with growth medium containing 800 µg/mL Geneticin (Gibco BRL). Surviving individual colonies were isolated and screened for VR1 receptor activity. Cells expressing recombinant homomeric VR1 receptors were maintained at 37° C. in D-MEM containing 4 mM L-glutamine, 300 µg/mL G418 (Cal-biochem) and 10% fetal bovine serum under a humidified 5% $CO_2$ atmosphere.

The functional activity of compounds at the VR1 receptor was determined with a $Ca^{2+}$ influx assay and measurement of intracellular $Ca^{2+}$ levels ($[Ca^{2+}]i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 µM solution of the VR1 agonist capsaicin was also prepared in D-PBS. The fluorescent $Ca^{2+}$ chelating dye fluo-4 was used as an indicator of the relative levels of $[Ca^{2+}]i$ in a 96-well format using a Fluorescence Imaging Plate Reader (FLIPR)(Molecular Devices, Sunnyvale, Calif.). Cells were grown to confluency in 96-well black-walled tissue culture plates. Then, prior to the assay, the cells were loaded with 100 µL per well of fluo-4 AM (2 µM, in D-PBS) for 1–2 hours at 23° C. Washing of the cells was performed to remove extracellular fluo-4 AM (2×1 mL D-PBS per well), and afterward, the cells were placed in the reading chamber of the FLIPR instrument. 50 µL of the compound solutions were added to the cells at the 10 second time mark of the experimental run. Then, after a 3 minute time delay, 50 µL of the capsaicin solution was added at the 190 second time mark (0.05 µM final concentration)(final volume=200 µL) to challenge the VR1 receptor. Time length of the experimental run was 240 seconds. Fluorescence readings were made at 1 to 5 second intervals over the course of the experimental run. The peak increase in relative fluorescence units (minus baseline) was calculated from the 190 second time mark to the end of the experimental run, and expressed as a percentage of the 0.05 µM capsaicin (control) response. Curve-fits of the data were solved using a four-parameter logistic Hill equation in GraphPad Prism® (GraphPad Software, Inc., San Diego, Calif.), and $IC_{50}$ values were calculated.

The compounds of the present invention were found to be antagonists of the vanilloid receptor subtype 1 (VR1) receptor with $IC_{50s}$, from about 69,000 nM to about 16 nM. In a preferred range, compounds tested had $IC_{50s}$ from about 500 nM to 0.1 nM. In a more preferred range, compounds tested had $IC_{50s}$, from 50 nM to 0.1 nM.

In Vivo Data

Determination of Antinociceptive Effect

Experiments were performed on 400 adult male 129J mice (Jackson laboratories, Bar Harbor, Me.), weighing 20–25 g. Mice were kept in a vivarium, maintained at 22° C., with a 12 hour alternating light-dark cycle with food and water available ad libitum. All experiments were performed during the light cycle. Animals were randomly divided into separate groups of 10 mice each. Each animal was used in one experiment only and was sacrificed immediately following the completion of the experiment. All animal handling and experimental procedures were approved by an IACUC Committee.

The antinociceptive test used was a modification of the abdominal constriction assay described in Collier, et al., Br. J. Pharmacol. Chemother. 32 (1968) 295–310. Each animal received an intraperitoneal (i.p.) injection of 0.3 mL of 0.6% acetic acid in normal saline to evoke writhing. Animals were placed separately under clear cylinders for the observation and quantification of abdominal constriction. Abdominal constriction was defined as a mild constriction and elongation passing caudally along the abdominal wall, accompanied by a slight twisting of the trunk and followed by bilateral extension of the hind limbs. The total number of abdominal constrictions was recorded from 5 to 20 minutes after acetic acid injection. The $ED_{50s}$ were determined based on the i.p. injection.

The compounds of the present invention were found to have antinociceptive effects with $ED_{50s}$ from about 500 mg/kg to about 0.1 mg/kg.

The in vitro and in vivo data demonstrates that compounds of the present invention antagonize the VR1 receptor and are useful for treating pain.

Compounds of the present invention, as VR1 antagonists, are also useful for ameliorating or preventing additional disorders that are affected by the VR1 receptors such as, but not limited to, inflammatory thermal hyperalgesia, bladder overactivity, and urinary incontinence.

Compounds of the present invention can be used to treat pain as demonstrated by Nolano, M. et al., Pain 81 (1999) 135; Caterina, M. J. and Julius, D., Annu. Rev. Neurosci. 24, (2001) 487–517; Caterina, M. J. et al., Science 288 (2000) 306–313; and Caterina, M. J. et al., Nature 389 (1997) 816–824.

Compounds of the present invention can be used to treat bladder overactivity and/or urinary incontinence as demonstrated by Fowler, C. Urology 55 (2000) 60.

Compounds of the present invention can be used to treat inflammatory thermal hyperalgesia as demonstrated by Davis, J. et al., Nature 405 (2000) 183–187.

The present invention also provides pharmaceutical compositions that comprise compounds of the present invention. The pharmaceutical compositions comprise compounds of the present invention formulated together with one or more non-toxic pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutically acceptable salt," as used herein, means salts derived from inorganic or organic acids. The salts can be prepared in situ during the final isolation and purification of compounds of formula (I) or separately by reacting the free base of a compound of formula (I) with an inorganic or organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, dihydrochloride, hydrobromide, hydroiodide, 2-hydroxyethansulfonate (isethionate), lactate, maleate, fumarate, methanesulfonate, nicotinate, 2-naphthalenesulfonate, oxalate, pamoate, pectinate, persulfate, 3-phenylpropionate, picrate, pivalate, propionate, succinate, sulfate, (L) tartrate, (D) tartrate, (DL) tartrate, thiocyanate, phosphate, glutamate, bicarbonate, p-toluenesulfonate, and undecanoate.

The term "pharmaceutically acceptable ester," as used herein, means esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods.

The term "pharmaceutically acceptable amide," as used herein, means to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, C1-to-$C_3$ alkyl primary amides and $C_1$-to-$C_2$ dialkyl secondary amides are preferred. Amides of the compounds of formula (I) may be prepared according to conventional methods.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like. Prodrugs of the present invention may be rapidly transformed in vivo to compounds of formula (I), for example, by hydrolysis in blood.

The present invention contemplates compounds of formula (I) formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The total daily dose of the compounds of this invention administered to a human or lower animal may range from about 0.01 to about 125 mg/kg/day. For purposes of oral administration, more preferable doses can be in the range of from about 0.1 to about 150 mg/kg/day. If desired, the effective daily dose can be divided into multiple doses for purposes of administration; consequently, single dose compositions may contain such amounts or submultiples thereof to make up the daily dose.

Abbreviations

Abbreviations which have been used in the descriptions of the Schemes and the Examples that follow are: Ac for acetyl; Bu for butyl; CyMAP for 2-dicyclohexylphosphino-2'-dimethylamino-1,1'-biphenyl; dba for dibenzylideneacetone; dppf for 1,1'-bis(diphenylphosphino)ferrocene; DBU for 1,8-diazabicyclo[5.4.0]undec-7-ene; DCC for 1,3-dicyclohexylcarbodiimide; DIEA for diisopropylethylamine; DMAP for 4-dimethylaminopyridine; DME for 1,2-dimethoxyethane; DMF for N,N-dimethylformamide; DMSO for dimethylsulfoxide; EDCI or EDC for 1-ethyl-3-[3-(dimethylamino)propyl]-carbodiimide hydrochloride; HObt for 1-hydroxybenzotriazole; HPLC high pressure liquid chromatography; NBS for N-bromosuccinimide; Ph for phenyl; psi for pounds per square inch; THF for tetrahydrofuran; Tf for $-S(O)_2CF_3$; and TMS for trimethylsilyl.

Preparation of Compounds of the Present Invention

The compounds and processes of the present invention will be better understood in connection with the following synthetic Schemes and Examples which illustrate a means by which the compounds of the present invention can be prepared. Further, all citations herein are incorporated by reference.

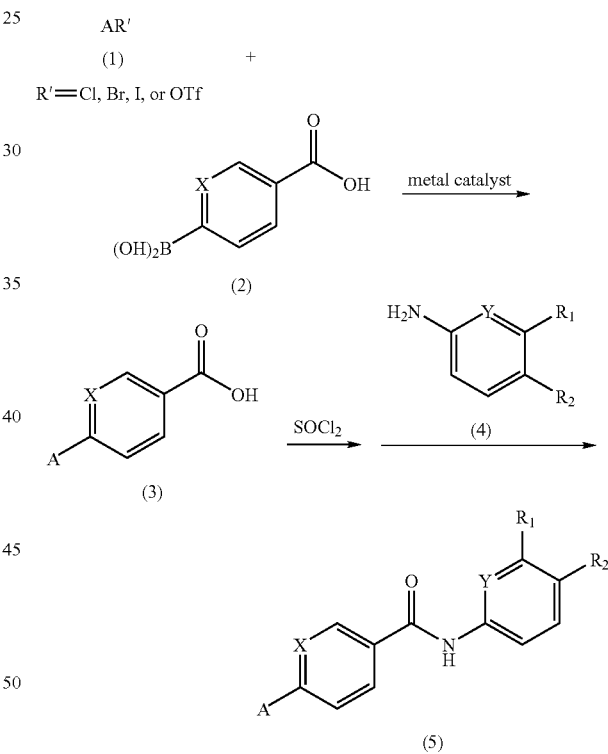

Scheme I

Amides of general formula (5), wherein A, X, Y, $R_1$, and $R_2$ are as defined in formula (I), can be prepared as described in Scheme 1. Aryl or heteroaryl compounds of general formula (1), wherein R' is Cl, Br, I, or triflate can be treated with boronic acids (or esters) of general formula (2), a palladium catalyst including, but not limited to Pd(Ph$_3$)$_4$, and a base including, but not limted to, sodium carbonate with heat in a solvent including, but not limited to acetonitrile, to provide acids of general formula (3). Acids of general formula (3) can be treated with thionyl chloride and anilines of general formula (4) to provide amides of general formula (5).

EXAMPLE 1

N-(4-tert-butylphenyl)-4-(2-pyridinyl)benzamide

EXAMPLE 1A 4-(2-pyridinyl)benzoic Acid

2-Bromopyridine (1.26 g, 7.97 mmol), 4-carboxyphenyl-boronic acid (1.32 g, 7.95 mmol), and Pd(PPh$_3$)$_4$ (0.48 g, 0.42 mmol) were stirred at 90° overnight in CH$_3$CN (40 mL) and 0.4 M Na$_2$CO$_3$ solution (40 mL, 16 mmol). After this time, the mixture was filtered hot, and the filtrate was concentrated to half-volume under reduced pressure. The remaining liquid was washed with CH$_2$Cl$_2$ (2×20 mL) and then acidified to pH 1 with concentrated HCl. The resulting precipitate was collected by filtration, washed with H$_2$O, and allowed to air-dry to provide the title compound. $^1$H NMR (300 MHz, DMSO-d$_6$) δ 8.74 (m, 1H), 8.19–8.23 (m, 2H), 7.99–8.12(m, 4H), 7.47–7.52 (m, 1H); MS (ESI$^+$) m/z 200 (M+H)$^+$.

EXAMPLE 1B

N-(4-tert-butylphenyl)-4-(2-pyridinyl)benzamide

The product from Example 1A (570 mg, 2.86 mmol) in SOCl$_2$ (10 mL) was refluxed for 1 hour. The solution was allowed to cool to room temperature and SOCl$_2$ was removed under reduced pressure. The residue was taken up in tetrahydrofuran (10 mL) and treated with DIEA (2.5 mL, 14.4 mmol, 5 eq) and 4tert-butylaniline (0.41 mL, 2.57 mmol). After stirring overnight at room temperature, the tetrahydrofuran was removed under reduced pressure and replaced with ethyl acetate (20 mL). The ethyl acetate was washed with H$_2$O and brine, dried (Na$_2$SO$_4$), filtered, and the filtrate concentrated under reduced pressure. The residue was chromatographed on silica gel (eluant gradient from 7:3 hexanes:ethyl acetate to 1:1 hexanes:ethyl acetate) to provide the title compound as a solid. $^1$H NMR (300 MHz, DMSO-d$_6$) δ 10.26 (s, 1H), 8.71–8.74 (m, 1H), 8.23–8.26 (m, 2H), 8.07–8.10 (m, 3H), 7.94 (td, j=7.4 Hz, 2.1 Hz, 1H), 7.70–7.73 (m, 2H), 7.37–7.44 (m, 3H), 1.29 (s, 9H); MS (ESI$^+$) m/z 331 (M+H)$^+$.

EXAMPLE 2

N-(4-tert-butylphenyl)-4-(3-nitro-2-pyridinyl)benzamide

The title compound was prepared using the procedures in Examples 1A and 1B replacing 2-bromopyridine with 3-nitro-2-bromopyridine. $^1$H NMR (300 MHz, DMSO-d$_6$) δ 10.32 (s, 1H), 8.97 (dd, J=4.7 Hz, 1.7 Hz, 1H), 8.52 (dd, 8.1 Hz, 1.4 Hz, 1H), 8.02–8.06 (m, 2H), 7.67–7.77 (m, 5H), 7.37–7.40 (m, 2H), 1.29 (s, 9H); MS (ESI$^+$) m/z 376 (M+H)$^+$.

EXAMPLE 3

4-(3-amino-2-pyridinyl)-N-(4-tert-butylphenyl)benzamide

The product from Example 2 (720 mg, 2.18 mmol) was hydrogenated (balloon apparatus) as a solution in 30 mL of 1:1 EtOH:CH$_2$Cl$_2$ over 10% Pd/C overnight at room temperature. The mixture was filtered through Celite and the filtrate was concentrated under reduced pressure to provide the title compound as a solid. $^1$H NMR (300 MHz, DMSO-d$_6$) δ 10.22 (s, 1H), 8.04–8.08 (m, 2H), 7.95 (dd, J=4.4 Hz, 1.7 Hz, 1H), 7.70–7.84 (m, 2H), 7.36–7.40 (m, 2H), 7.19 (dd, j=8.2 Hz, 1.7 Hz, 1H), 7.11 (dd, J=8.1 Hz, 4.4 Hz, 1H), 1.29 (s, 9H); MS (ESI$^+$) m/z 346 (M+H)$^+$.

EXAMPLE 4

N-(4-tert-butylphenyl)-4-(1H-tetraazol-5-yl)benzamide

EXAMPLE 4A

N-(4-tert-butylphenyl)-4-cyanobenzamide 4-cyanobenzoyl chloride (2 g, 12.08 mmol), DIEA (7.3 mL, 42 mmol), and 4-tert-butylaniline (1.9 mL, 11.9 mmol) were stirred in tetrahydrofuran (50 mL) overnight at room temperature. The tetrahydrofuran was removed under reduced pressure and replaced with ethyl acetate. The ethyl acetate was washed with H$_2$O and brine, dried over Na$_2$SO$_4$, filtered, and the filtrate concentrated under reduced pressure. The residue was purified by column chromatography on silica gel (eluant gradient from 8:2 hexanes:ethyl acetate to 1:1 hexanes:ethyl acetate) to afford the title compound as a solid. $^1$H NMR (300 MHz, DMSO-d$_6$) δ 10.41 (s, 1H), 8.08–8.12 (m, 2H), 8.01–8.04 (m, 2H), 7.66–7.69 (m, 2H), 7.37–7.41 (m, 2H), 1.28 (s, 9H); MS (ESI$^+$) m/z 279 (M+H)$^+$.

EXAMPLE 4B

N-(4-tert-butylphenyl)-4-(1H-tetraazol-5-yl)benzamide

The product from Example 4A (300 mg, 1.08 mmol) in N,N-dimethylacetamide (10 mL) was treated with NaN$_3$ (0.7 g, 10.8 mmol) and MgCl$_2$ (1.03 g, 10.8 mmol). The mixture was heated at 150° C. for 16 hours, allowed to cool to room temperature, and poured into H$_2$O (50 mL). The mixture was filtered and the filter cake air-dried to provide the title compound as a solid. $^1$H NMR (300 MHz, DMSO-d$_6$) δ 10.14 (s, 1H), 8.10 (d, J=8.4 Hz, 2H), 7.97 (d, j=8.4 Hz, 2H), 7.71 (d, J=8.5 Hz, 2H), 7.36 (d, J=8.4 Hz, 2H), 1.29 (s, 9H); MS (ESI$^+$) $^{m/z}$ 322 (M+H)$^+$.

EXAMPLE 5

4-[3-(acetylamino)-2-pyridinyl]-N-(4-tert-butylphenyl)benzamide

The product from Example 3 (150 mg, 0.435 mmol) in acetic anhydride (0.24 mL, 2.54 mmol) was heated in tetrahydrofuran (2 mL) at 40° C. overnight. The mixture was allowed to cool to room temperature and concentrated under reduced pressure to provide the title compound as a solid. $^1$H NMR (300 MHz, DMSO-d$_6$) δ 10.25 (s, 1H), 9.68 (s, 1H), 8.53 (dd, J=4.6 Hz, 1.5 Hz, 1H), 8.06 (m, 2H), 7.91 (dd, J=8.1 Hz, 1.3 Hz, 1H), 7.7–7.78 (m, 4H), 7.36–7.45 (m, 3H), 1.97 (s, 3H), 1.29 (s, 9H); MS (ESI$^{30}$) m/z 388 (M+H)$^+$.

EXAMPLE 6

N-(4-tert-butylphenyl)-4-(1H-imidazol-2-yl)benzamide

The title compound was prepared using the procedure in Example 1B and replacing 4-(1H-imidazol-2-yl)benzoic acid for the product from Example 1A. $^1$H NMR (300 MHz, DMSO-$d_6$) δ 12.70 (s, 1H), 10.18 (s, 1H), 8.00–8.10 (m, 4H), 7.67–7.72 (m, 2H), 7.33 (br s, 1H), 7.09 (br s, 1H), 1.29 (s, 9H); MS (ESI$^+$) m/z 320 (M+H)$^+$.

EXAMPLE 7

4-{3-[bis(methylsulfonyl)amino]-2-pyridinyl}-N-(4-tert-butylphenyl)benzamide

The product from Example 3 (300 mg, 0.87 mmol) and triethylamine (0.6 mL, 4.3 mmol) in $CH_2Cl_2$ (10 mL) were treated with methanesulfonyl chloride (0.2 mL, 2.58 mmol) at room temperature and stirred overnight. The reaction mixture was diluted with $CH_2Cl_2$ (20 mL), washed with $H_2O$ (3×5 mL) and brine (5 mL), dried over $Na_2SO_4$, filtered, and the filtrate concentrated under reduced pressure. The residue was purified by column chromatography on silica gel (99:1 $CH_2Cl_2$:$CH_3OH$) to provide the title compound as a solid. $^1$H NMR (300 MHz, DMSO-$d_6$) δ 10.30 (s, 1H), 8.81 (dd, J=4.6 Hz, 1.6 Hz, 1H), 8.25 (dd, J=8.1 Hz, 1.4 Hz, 1H), 8.11–8.14 (m, 2H), 7.61–7.77 (m, 5H), 7.37–7.41 (m, 2H), 3.19 (s, 6H), 1.29 (s, 9H); MS (ESI$^+$) m/z 502 (M+H)$^+$.

EXAMPLE 8

N-(4-tert-butylphenyl)-4-(1,3-thiazol-2-yl)benzamide

The title compound was prepared using the procedures in Examples 1A and 1B replacing 2-bromopyridine with 2-bromothiazole. $^1$H NMR (300 MHz, DMSO-$d_6$) δ 10.29 (s, 1H), 8.09 (m, 4H), 8.01 (d, J=3.0 Hz, 1H), 7.90 (d, J=3.0 Hz, 1H), 7.69–7.72 (m, 2H), 7.37–7.39 (m, 2H), 1.29 (s, 9H); MS (ESI$^+$) m/z 337 (M+H)$^+$.

EXAMPLE 9

N-(4-tert-butylphenyl)-4-(2-pyrimidinyl)benzamide

The title compound was prepared using the procedures in Examples 1A and 1B replacing 2-bromopyridine with 2-bromopyrimidine. $^1$H NMR (300 MHz, DMSO-$d_6$) δ 10.31 (s, 1H), 8.97 (d, J=4.8 Hz, 2H), 8.51–8.54 (m, 2H), 8.09–8.13 (m, 2H), 7.69–7.74 (m, 2H), 7.52 (t, j=4.9 Hz, 1H), 7.36–7.41 (m, 2H), 1.29 (s, 9H); MS (ESI$^+$) m/z 332 (M+H)$^+$.

EXAMPLE 10

N-[3-fluoro-4-(1-piperidinyl)phenyl]-4-(2-pyridinyl)benzamide

EXAMPLE 10A 1-(2-fluoro-4-nitrophenyl)piperidine 3,4-Difluoronitrobenzene (1.4 mL, 2.01 g, 12.7 mmol) in piperidine (4 mL, 40.4 mmol) was heated in a sealed tube at 130° C. for 2 hours. The mixture was allowed to cool to room temperature and poured into $H_2O$ (150 mL). The title compound was separated by pipette. $^1$H NMR (300 MHz, DMSO-$d_6$) δ 7.95–8.01 (m, 2H), 7.11–7.18 (m, 1H), 3.26–3.29 (m, 4H), 1.62–1.68 (m, 6H); MS (ESI$^+$) m/z 225 (M+H)$^+$.

EXAMPLE 10B 3-fluoro-4-(1-piperidinyl)Aniline

The product from Example 10A (12.7 mmol) was hydrogenated (balloon) as a solution in ethyl acetate over 5% Pd/C overnight at room temperature. The mixture was filtered through Celite and the filtrate was concentrated under reduced pressure to provide the title compound. $^1$H NMR (300 MHz, DMSO-$d_6$) δ 6.72–6.78 (m, 1H), 6.26–6.34 (m, 2H), 4.92 (br s, 2H), 2.76 (m, 4H), 1.56–1.63 (m, 4H), 1.42–1.49 (m, 2H); MS (APCI$^+$) m/z 195.

EXAMPLE 10C

N-[3-fluoro-4-(1-piperidinyl)phenyl]-4-(2-pyridinyl)benzamide 4-(Pyrid-2-yl)benzoyl chloride (1.37 mmol, prepared as described in Example 1B, and DIEA (1.2 mL, 6.9 mmol) in tetrahydrofuran (5 mL) were treated with the product from Example 10B (260 mg, 1.34 mmol). The mixture was stirred overnight at room temperature and concentrated under reduced pressure. The residue was taken up in ethyl acetate (50 mL), washed with $H_2O$ (3×15 mL) and brine (15 mL), dried over $Na_2SO_4$, filtered, and the filtrate was concentrated under reduced pressure. The residue was triturated with 3:2 hexanes:ethyl acetate to provide the title compound as a solid. $^1$H NMR (300 MHz, DMSO-$d_6$) δ 10.32 (s, 1H), 8.72 (d, J=4.7 Hz, 1H), 8.25 (d, J=8.2 Hz, 2H), 8.05–8.10 (m, 3H), 7.94 (td, J=7.8 Hz, 1.7 Hz, 1H), 7.70 (dd, J=14.9 Hz, 2.4 Hz, 1H), 7.40–7.50 (m, 2H), 7.04 (t, J=9.4 Hz, 1H), 2.92–2.96 (m, 4H), 1.62–1.69 (m, 4H), 1.52–1.56 (m, 2H); MS (ESI$^+$) m/z 376 (M+H)$^+$.

EXAMPLE 11

N-(4-tert-butylphenyl)-4-(3-cyano-2-pyridinyl)benzamide

The title compound was prepared using the procedures in Examples 1A and 1B replacing 2-bromopyridine with 2-chloro-3-cyanopyridine. $^1$H NMR (300 MHz, DMSO-$d_6$) δ 10.36 (s, 1H), 8.98 (dd, J=4.8 Hz, 1.7 Hz, 1H), 8.49 (dd, J=7.8 Hz, 1.7 Hz, 1H), 8.11–8.14 (m, 2H), 8.00–8.02 (m, 2H), 7.65–7.74 (m, 3H), 7.37–7.40 (m, 2H), 129 (s, 9H); MS (ESI$^+$) m/z 356 (M+H)$^+$.

EXAMPLE 12

N-(4-tert-butylphenyl)-6-phenylnicotinamide

EXAMPLE 12A 5-methyl-2-phenylpyridine

Phenylboronic acid (732 mg, 6 mmol), 2-bromo-5-methylpyridine (1.03g, 5.99 mmol), and Pd (PPh$_3$)$_4$ (350 mg, 0.303 mmol) were heated in 0.4 M $K_2CO_3$ (30 mL, 12 mmol) and $CH_3CN$ (30 mL) at 90° overnight. The mixture was then cooled to room temperature and concentrated under reduced pressure. The residue was partitioned between brine and ethyl acetate. The organic layer was separated, dried ($Na_2SO_4$, filtered, and the filtrate was concentrated under reduced pressure. The residue was purified by column chromatography on silica gel (9:1 hexanes:ethyl acetate) to provide the title compound. $^1$H NMR (300 MHz, DMSO-$d_6$) δ 8.50 (m, 1H), 8.05 (m, 2H), 7.85 (d, J=8.4 Hz, 1H), 7.68–7.71 (m, 1H), 7.37–7.50 (m, 3 H), 2.34 (s, 3H); MS (APCI$^+$) m/z 170 (M+H)$^+$.

EXAMPLE 12B

6-phenylnicotinic Acid

The product from Example 12A (710 mg, 4.2 mmol) was treated with KMnO$_4$ (1.33 g) as described in Can. J. Chem., 38:768 (1960) to provide the title compound as a solid. $^1$H NMR (300 MHz, DMSO-$d_6$) δ 9.15 (dd, J=2.3 Hz, 0.7 Hz, 1H), 8.33 (dd, J=8.3 Hz, 2.2 Hz, 1H), 8.10–8.18 (m, 3H), 7.52–7.54 (m, 3H); MS (ESI$^+$) m/z 200 (M+H)$^+$.

EXAMPLE 12C

N-(4-tert-butylphenyl)-6-phenylnicotinamide

The title compound was prepared using the procedure in Example 1B replacing the product from Example 1A with the product from Example 12B. $^1$H NMR (300 MHz, DMSO-$d_6$) δ 10.39 (s, 1H), 9.19 (m, 1H), 8.39 (dd, J=8.1 Hz, 2.3 Hz, 1H), 8.13–8.20 (m, 2H), 7.69–7.72 (m, 2H), 7.50–7.58 (m, 2H), 7.38–7.41 (m, 2H), 7.02 (m, 1H), 6.49 (m, 1H), 1.29 (s, 9H); MS (ESI$^+$) m/z 331 (M+H)$^+$.

EXAMPLE 13

N-(4-tert-butylphenyl)-4-(2-thienyl)benzamide

The title compound was prepared using the procedures in Examples 1A and 1B replacing 2-bromopyridine with 2-bromothiophene. $^1$H NMR (300 MHz, DMSO-$d_6$) δ 10.19 (s, 1H), 8.00 (m, 2H), 7.82 (m, 2H), 7.64–7.71 (m, 4H), 7.35–7.40 (m, 2H), 7.18–7.24 (m, 1H), 1.29 (s, 9H); MS (ESI$^+$) m/z 336 (M+H)$^+$.

EXAMPLE 14

4-{3-[acetyl(methylsulfonyl)amino]-2-pyridinyl}-N-(4-tert-butylphenyl)benzamide The product from Example 5 (610 mg, 1.58 mmol) in tetrahydrofuran (10 mL) was treated with n-BuLi (1.1 mL, 1.6 M in hexanes, 1.76 mmol) dropwise at −10° C. The reaction mixture was stirred at −10° C. for 15 minutes and then treated with methanesulfonyl chloride (0.13 mL, 1.68 mmol). The mixture was allowed to gradually warm to room temperature and stir overnight, quenched with H$_2$O (10 mL), and diluted with ethyl acetate (50 mL). The layers were separated and the organic layer was washed with H$_2$O (2×10 mL) and brine (10 mL), dried (Na$_2$SO$_4$), filtered, and the filtrate concentrated under reduced pressure. The residue was purified by chromatography on silica gel (eluant gradient from 99:1 CH$_2$Cl$_2$:CH$_3$OH to 97:3 CH$_2$Cl$_2$:CH$_3$OH) to provide the title compound as a solid. $^1$H NMR (300 MHz, DMSO-$d_6$) δ 10.29 (s, 1H), 8.81 (dd, J=4.7 Hz, 1.7 Hz, 1H), 8.15 (dd, J=8.2 Hz, 1.7 Hz, 1H), 8.07 (m, 2H), 7.62–7.73 (m, 5H), 7.35–7.40 (m, 2H), 3.30 (s, 3H), 2.01 (s, 3H), 1.29 (s, 9H); MS (ESI$^+$) m/zδ 466 (M+H)$^+$.

EXAMPLE 15

4-(6-bromo-2-pyridinyl)-N-(4-tert-butylphenyl)benzamide

The title compound was prepared using the procedures in Examples 1A and 1B replacing 2-bromopyridine with 2,6-dibromopyridine. $^1$H NMR (300 MHz, DMSO-$d_6$) δ 10.29 (s, 1H), 8.08–8.22 (m, 5H), 7.90 (t, J=8.0 Hz, 1H), 7.72 (m, 3H), 7.38 (m, 2H), 1.29 (s, 9H); MS (ESI$^+$) m/z 410 (M+H)$^+$.

EXAMPLE 16

Methyl 2-(4-{[(4-tert-butylphenyl)amino]carbonyl}phenyl)-3-pyridinylcarbamate The product from Example 3 (500 mg, 1.45 mmol), methyl chloroformate (0.43 mL, 5.56 mmol), and K$_2$CO$_3$ (1.15 g, 8.33 mmol) were heated in DME (8 mL) at 65° C. for 24 hours. The mixture was allowed to cool to room temperature, concentrated under reduced pressure, and the residue was taken up in ethyl acetate (50 mL). The ethyl acetate was washed with H$_2$O (3×15 mL) and brine (15 mL), dried over Na$_2$SO$_4$, filtered, and the filtrate concentrated under reduced pressure. The residue was purified by column chromatography on silica gel (eluant gradient from 99:1 CH$_2$Cl$_2$:CH$_3$OH to 95:5 CH$_2$Cl$_2$:CH$_3$OH) to provide the title compound as a solid. $^1$H NMR (300 MHz, DMSO-$d_6$) δ 10.24 (s, 1H), 9.15 (s, 1H), 8.53 (dd, J=4.5 Hz, 1.6 Hz 1H), 8.02–8.05 (m, 2H), 7.88 (dd, J=8.1 Hz, 1.4 Hz, 1H), 7.70–7.77 (m, 4H), 7.35–7.46 (m, 3H), 3.55 (s, 3H), 1.29 (s, 9H); MS (ESI$^+$) m/z 404 (M+H)$^+$.

EXAMPLE 17

4-(3-{bis[(chloromethyl)sulfonyl]amino}-2-pyridinyl)-N-(4-tert-butylphenyl)benzamide The product from Example 3 (500 mg, 1.45 mmol), chloromethanesulfonyl chloride (0.65 g, 4.36 mmol), and triethylamine (1 mL, 7.19 mmol) were stirred in CH$_2$Cl$_2$ (15 mL) overnight at room temperature. The reaction mixture was then diluted with CH$_2$Cl$_2$, washed with H$_2$O and brine, dried over Na$_2$SO$_4$, filtered, and the filtrate concentrated under reduced pressure. The residue was purified by column chromatography on silica gel (99:1 CH$_2$Cl$_2$:CH$_3$OH, eluant) to provide the title compound as a solid. $^1$ NMR (300 MHz, DMSO-$d_6$) δ 10.31 (s, 1H), 8.87 (dd, J=4.7 Hz, 1.3 Hz, 1H), 8.32 (dd, J=8.2 Hz, 1.7 Hz, 1H), 8.14 (d, J=8.5 Hz, 2H), 7.68–7.77 (m, 3H), 7.38 (d, J=8.8 Hz, 2H), 5.46 (s, 1H), 5.42 (s, 1H), 4.97 (s, 1H), 4.92 (s, 1H), 1.29 (s, 9H).

EXAMPLE 19

N-(4-tert-butylphenyl)-4-(1 H-pyrazol-1-yl)benzamide 4-(1-Pyrazoyl)benzoic acid (1.17 g, 6.22 mmol), prepared according to J. Am. Chem. Soc., 3997 (1949); Chem. Ber., 23:1452 (1890), was refluxed in SOCl$_2$ (10 mL) for 90 minutes, allowed to cool to room temperature, and concentrated under reduced pressure. The residue was dissolved in tetrahydrofuran (25 mL) and was treated with DIEA (5.3 mL, 30.5 mmol) and 4-tert-butylaniline (1 mL, 6.28 mmol). After stirring overnight at room temperature, the mixture was concentrated under reduced pressure and the residue was dissolved in ethyl acetate. The ethyl acetate was washed with H$_2$O and brine, dried over Na$_2$SO$_4$, filtered, and the filtrate concentrated under reduced pressure. The residue was purified by column chromatography on silica gel (eluant gradient from 85:15 hexanes:ethyl acetate to 80:20 hexanes: ethyl acetate) to provide the title compound as a solid. $^1$H NMR (300 MHz, DMSO-d$_6$) δ 10.21 (s, 1H), 8.64 (m, 1H), 8.08–8.12 (m, 2H), 7.99–8.03 (m, 2H), 7.82 (d, J=1.7 Hz, 1H), 7.67–7.71 (m, 2H), 7.35–7.40 (m, 2H), 6.61 (m, 1H), 1.29 (s, 9H); MS (ESI$^+$) m/z 320 (M+H)$^+$.

EXAMPLE 20

N-(4-tert-butylphenyl)-4-(3-pyridinyl)benzamide

The title compound was prepared using the procedures in Examples 1A and 1B replacing 2-bromopyridine with 3-bromopyridine. $^1$H NMR (300 MHz, DMSO-d$_6$) δ 10.25 (s, 1H), 9.00 (d, J=2.4 Hz, 1H), 8.61 (dd, J=4.7 Hz, 1.7 Hz, 1H), 8.18 (dt, J=8.1 Hz, 1.6 Hz, 1H), 8.09 (m, 2H), 7.92 (m, 2H), 7.72 (m, 2H), 7.54 (m, 1H), 7.38 (m, 2H), 1.29 (s, 9H); MS (ESI$^+$) m/z 331 (M+H)$^+$.

EXAMPLE 21

N-(4-tert-butylphenyl)-6-(1H-pyrazol-1-yl)nicotinamide

EXAMPLE 21A

N-(4-tert-butylphenyl)-6-chloronicotinamide

2-Chloronicotinyl chloride (1.76 g, 10 mmol), 4-tert-butylphenylamine (1.49 g, 10 mmol), and triethylamine (2 g) were combined in CHCl$_3$ (100 mL) and stirred at room temperature overnight. The mixture was washed with saturated Na$_2$CO$_3$ solution (40 mL), dried over MgSO$_4$, filtered, and the filtrate was concentrated to dryness under reduced pressure. The title compound was used in the next step without further purification.

EXAMPLE 21B

N-(4-tert-butylphenyl)-6-(1H-pyrazol-1-yl)nicotinamide

Pyrazole (0.34 g, 5 mmol) in 10 mL of DMF was treated with sodium hydride (0.2 g in 60% mineral oil) at room temperature. The mixture was then treated with the product from Example 21A in DMF (20 mL) and heated at 100° C. for 4 hours. The reaction mixture was allowed to cool to room temperature and quenched with water. The mixture was filtered and the filter cake was collected as the title compound. $^1$H NMR (300 MHz, DMSO-d$_6$) δ 10.39 (bs, 1H), 9.01 (dd, 1H), 8.71 (dd, 1H), 8.52 (dd, 1H), 8.07 (d, 1H), 7.7 (m, 1H), 7.65 (m, 2H), 7.4 (m, 2H), 6.6 (m, 1H) 1.25 (s, 9H); MS (ESI$^+$) m/z 321 (M+H)$^+$.

EXAMPLE 22

N-(4-tert-butylphenyl)-4-(4-pyridinyl)benzamide

The title compound was prepared using the procedures in Examples 1A and 1B replacing 2-bromopyridine with 4-bromopyridine. $^1$H NMR (300 MHz, DMSO-d$_6$) δ 10.28 (s, 1H), 8.69 (m, 1H), 8.10 (m, 2H), 7.98 (m, 2H), 7.80 (m, 2H), 7.72 (m, 2H), 7.38 (m, 2H), 7.38 (m, 2H), 1.29 (s, 9H); MS (ESI$^+$) m/z 331 (M+H)$^+$.

EXAMPLE 23

N-(4-tert-butylphenyl)-4-(1,3-oxazol-2-yl)benzamide

EXAMPLE 23A

Methyl 4-{[(4-tert-butylphenyl)amino]carbonyl}benzoate mono-Methyl terephthalate (1.02 g, 5.67 mmol) was refluxed in SOCl$_2$ (10 mL) for 1 hour, allowed to cool to room temperature, and concentrated under reduced pressure. The residue was taken up in tetrahydrofuran (30 mL) and treated with 4tert-butylaniline (0.9 mL, 5.65 mmol) and DIEA (5 mL, 28.8 mmol) at room temperature. After stirring overnight, the mixture was concentrated under reduced pressure and the residue was taken up in ethyl acetate. The ethyl acetate was washed with H$_2$O and brine, dried over Na$_2$SO$_4$, filtered, and the filtrate was concentrated under reduced pressure. The residue was triturated with 3:2 hexanes:ethyl acetate and the solid air-dried to provide the title compound. $^1$H NMR (300 MHz, DMSO-d$_6$) δ 10.37 (s, 1H), 8.08 (m, 4H), 7.69 (m, 2H), 7.39 (m, 2H), 3.90 (s, 3H), 1.29 (s, 9H); MS (ESI$^-$) m/z 312 (M+H)$^+$.

EXAMPLE 23B

4-{[(4-tert-butylphenyl)amino]carbonyl}benzoic Acid

The product from Example 23A (0.71 g, 2.28 mmol) in tetrahydrofuran (23 mL) and CH$_3$OH (5.7 mL) was treated with 1N aqueous LiOH (5.7 mL, 5.7 mmol). After stirring overnight at room temperature, the organic solvents were removed under reduced pressure and the remaining aqueous solution was acidified to pH 1 with concentrated HCl. The acidified solution was extracted with ethyl acetate. The extracts were combined, dried over Na$_2$SO$_4$, filtered, and the filtrate concentrated under reduced pressure to provide the title compound as a solid. $^1$H NMR (300 MHz, DMSO-d$_6$) δ 10.33 (s, 1H), 8.06 (m, 4H), 7.69 (m, 2H), 7.38 (m, 2H), 1.29 (s, 9H); MS (ESI$^+$) m/z 298 (M+H)$^+$.

EXAMPLE 23C

N-(4-tert-butylphenyl)-4-(1,3-oxazol-2-yl)benzamide

The product from Example 23B (250 mg, 0.84 mmol) was refluxed for 1 hour with SOCl$_2$ (8 mL). After cooling to room temperature, the SOCl$_2$ was removed under reduced pressure and the residue was taken up in sulfolane (11 mL) and treated with 1H-1,2,3-triazole (0.045 mL, 53 mg, 0.78 mmol) and K$_2$CO$_3$ (230 mg, 1.67 mmol). The mixture was stirred for 20 hours at 140° C., allowed to cool to room temperature, and partitioned between ethyl acetate (60 mL) and H$_2$O (60 mL). The aqueous phase was extracted with ethyl acetate (3×20 mL) and all the organics were combined. The combined organics were washed with H$_2$O and brine, dried over Na$_2$SO$_4$, filtered, and the filtrate concentrated under reduced pressure. The residue was purified by column chromatography on silica gel (eluant: 75:25 hexanes:ethyl acetate) to provide the title compound as a solid. $^1$H NMR (300 MHz, DMSO-d$_6$) δ 10.31 (s, 1H), 8.30 (m, 1H), 8.11 (m, 4H), 7.70 (m, 2H), 7.45 (m, 1H), 7.38 (m, 2H), 1.29 (s, 9H); MS (ESI$^+$) m/z 321 (M+H)$^+$.

EXAMPLE 24

N-(4-tert-butylphenyl)-4-(3-chloro-2-pyridinyl)benzamide

EXAMPLE 24A 4-(3-chloro-2-pyridinyl)benzoic Acid 2,3-Dichloropyridine (2.66 g, 18.0 mmol), 4-carboxyphenylboronic acid (2.70 g, 16.3 mmol), and Pd(PPh$_3$)$_4$ (0.965 g, 0.835 mmol) were combined in a degassed solution of 1:1 0.5M aq Na$_2$CO$_3$:MeCN (120 mL), heated to 85° C. for 5 hours, filtered, and the filtrate concentrated under reduced pressure to remove most of the MeCN. The concentrate was extracted with CH$_2$Cl$_2$ (10 mL) and acidified with 1N HCl. The acidified solution was filtered and the filter cake dried under reduced pressure to provide the title compound as a solid.

EXAMPLE 24B

N-(4-tert-butylphenyl)-4-(3-chloro-2-pyridinyl)benzamide

The product from Example 24A (75.0 mg, 0.321 mmol), 4tert-butylaniline (61 μL, 0.383 mmol), PS-DCC (1.35 mmol/g, 0.7132 g, 0.963 mmol), HOBT (44.0 mg, 0.326 mmol), and triethylamine (0.13 mL, 0.93 mmol) in DMF (3 mL) were combined and heated at 55° C. for 16 hours. The mixture was allowed to cool to room temperature, filtered, and the filtrate was diluted with diethyl ether (20 mL). The diethyl ether was washed with 1N HCl (15 mL), brine (15 mL), dried (Na$_2$SO$_4$), filtered, and the filtrate concentrated under reduced pressure. The residue was purified by flash chromatography (30% ethyl acetate in hexanes) to provide the title compound. $^1$H NMR (300 MHz, CDCl$_3$) δ 8.63 (dd, 1H), 7.98 (d, 2H), 7.88 (d, 2H), 7.88 (d, 1H), 7.81 (br s, 1H), 7.59 (d, 2H), 7.41 (d, 2H), 7.29 (dd, 1H), 1.33 (s, 9H); MS (m/z) 365.

EXAMPLE 25

4-(3-chloro-2-pyridinyl)-N-[4-(1-pyrrolidinyl)phenyl]benzamide

The title compound was prepared using the procedure in Example 24B replacing 4-tert-butylaniline with 4-(1-pyrrolidinyl)aniline. $^1$H NMR (300 MHz, CDCl$_3$) δ 8.63 (d, 1H), 7.97 (d, 2H), 7.82–7.86 (m, 3H), 7.71 (br s, 1H), 7.48 (d, 2H), 7.28 (dd, 1H), 6.58 (d, 2H), 3.30 (m, 4H), 2.02 (m, 4H); MS (m/z) 378.

EXAMPLE 26

4-(3-chloro-2-pyridinyl)-N-[4-(1-piperidinyl)phenyl]benzamide

The title compound was prepared using the procedure in Example 24B replacing 4-tert-butylaniline with 4-(1-piperidinyl)aniline. $^1$H NMR (300 MHz, CDCl$_3$) δ 8.62 (dd, 1H), 7.96 (d, 2H), 7.86 (d, 2H), 7.83 (dd, 1H), 7.75 (br s, 1H), 7.52 (d, 2H), 7.27 (dd, 1H), 6.96 (d, 2H), 3.14 (t, 4H), 1.73 (m, 4H), 1.58 (m, 2H); MS (m/z) 392.

EXAMPLE 27

N-[4-(1-azepanyl)phenyl]-4-(3-chloro-2-pyridinyl)benzamide

The title compound was prepared using the procedure in Example 24B replacing 4-tert-butylaniline with 4-(1-azepanyl)aniline. $^1$H NMR (300 MHz, CDCl$_3$) δ 8.62 (dd, 1H), 7.96 (d, 2H), 7.84 (d, 2H), 7.82 (dd, 1H), 7.70 (br s, 1H), 7.45 (d, 2H), 7.27 (dd, 1H), 6.68 (d, 2H), 3.47 (t, 4H), 1.79 (m, 4H), 1.55 (m, 4H); MS (m/z) 406.

EXAMPLE 28

4-(3-chloro-2-pyridinyl)-N-(3-methylphenyl)benzamide

The title compound was prepared using the procedure in Example 24B replacing 4-tert-butylaniline with m-toluidine. $^1$H NMR (300 MHz, DMSO-d$_6$) δ 10.26 (s, 1H), 8.68 (dd, 1H), 8.09 (dd, 1H), 8.05 (d, 2H), 7.83 (d, 2H), 7.65 (s, 1H), 7.58 (d, 1H), 7.50 (dd, 1H), 7.24 (t, 1H), 6.94 (d, 1H), 2.32 (s, 3H); MS (m/z) 323.

EXAMPLE 29

4-(3-chloro-2-pyridinyl)-N-(4-methylphenyl)benzamide

The title compound was prepared using the procedure in Example 24B replacing 4-tert-butylaniline with p-toluidine. $^1$H NMR (300 MHz, DMSO) δ 10.26 (s, 1H), 8.67 (dd, 1H), 8.09 (dd, 1H), 8.05 (d, 2H), 7.82 (d, 2H), 7.68 (d, 2H), 750 (dd, 1H), 7.17 (d, 2H), 2.29 (s, 3H).

EXAMPLE 30

4-(3-chloro-2-pyridinyl)-N-(4-methoxyphenyl)benzamide

The title compound was prepared using the procedure in Example 24B replacing 4-tert-butylaniline with 4-methoxyaniline. $^1$H NMR (300 MHz, DMSO-d$_6$) δ 10.22 (s, 1H), 8.67 (dd, 1H), 8.09 (dd, 1H), 8.05 (d, 2H), 7.82 (d, 2H), 7.70 (d, 2H), 7.50 (dd, 1H), 6.94 (d, 2H), 3.76 (s, 3H); MS (m/z) 339.

EXAMPLE 31

4-(3-chloro-2-pyridinyl)-N-[3-(trifluoromethoxy)phenyl]benzamide

The title compound was prepared using the procedure in Example 24B replacing 4-tert-butylaniline with 3-(trifluoromethoxy)aniline. $^1$H NMR (300 MHz, DMSO-d$_6$) δ 10.60 (s, 1H), 8.67 (dd, 1H), 8.10 (dd, 1H), 8.07 (d, 2H), 7.97 (s, 1H), 7.85 (d, 2H), 7.80 (d, 1H), 7.50 (m, 2H), 7.11 (d, 1H); MS (m/z) 393.

EXAMPLE 32

4-(3-chloro-2-pyridinyl)-N-(4-phenoxyphenyl)benzamide

The title compound was prepared using the procedure in Example 24B replacing 4-tert-butylaniline with 4-phenoxyaniline. $^1$H NMR (300 MHz, DMSO-d$_6$) δ 10.38 (s, 1H), 8.67 (dd, 1H), 8.09 (dd, 1H), 8.06 (d, 2H), 7.83 (d, 2H), 7.82 (d, 2H), 7.50 (dd, 1H), 7.39 (t, 2H), 7.12 (t, 1H), 7.05 (d, 2H), 7.00 (d, 2H); MS (m/z) 401.

EXAMPLE 33

4-(3-chloro-2-pyridinyl)-N-(3,4-dimethylphenyl) benzamide

The title compound was prepared using the procedure in Example 24B replacing 4-tert-butylaniline with 3,4-dimethylaniline. $^1$H NMR (300 MHz, DMSO-$d_6$) δ 10.18 (s, 1H), 8.67 (dd, 1H), 8.09 (dd, 1H), 8.05 (d, 2H), 7.82 (d, 2H), 7.58 (s, 1H), 7.48–7.52 (m, 2H), 7.11 (d, 1H), 2.23 (s, 3H), 2.20 (s, 3H); MS (m/z) 337.

EXAMPLE 34

4-(3-chloro-2-pyridinyl)-N-(4-ethylphenyl)benzamide

The title compound was prepared using the procedure in Example 24B replacing 4-tert-butylaniline with 4-ethylaniline. $^1$H NMR (300 MHz, DMSO-$d_6$) δ 10.27 (s, 1H), 8.67 (dd, 1H), 8.09 (dd, 1H), 8.05 (d, 2H), 7.82 (d, 2H), 7.70 (d, 2H), 7.50 (dd, 1H), 7.20 (d, 2H), 2.59 (q, 2H), 1.19 (t, 3H); MS (m/z) 337.

EXAMPLE 35

4-(3-chloro-2-pyridinyl)-N-(4-isopropylphenyl)benzamide

The title compound was prepared using the procedure in Example 24B replacing 4-tert-butylaniline with 4-isopropylaniline. $^1$H NMR (300 MHz, DMSO-$d_6$) δ 10.27 (s, 1H), 8.67 (dd, 1H), 8.09 (dd, 1H), 8.05 (d, 2H), 7.82 (d, 2H), 7.70 (d, 2H), 7.50 (dd, 1H), 7.23 (d, 2H), 2.88 (t, 1H), 1.21 (d, 6H); MS (m/z) 351.

EXAMPLE 36

N-(4-tert-butylphenyl)-4-[1-(methylsulfonyl)-1H-imidazol-2-yl]benzamide

The product from Example 6 (71.4 mg, 0.224 mmol) and triethylamine (62 µL, 0.44 mmol) in CH$_2$Cl$_2$ (2 mL) at 0° C. were treated with methanesulfonyl chloride (21 µL, 0.27 mmol). The solution was stirred for 40 minutes, allowed to warm over 15 minutes, diluted with water (3 mL) and 1 N HCl (0.5 mL), and extracted with CH$_2$Cl$_2$ (3×4 mL). The extracts were combined, dried (Na$_2$SO$_4$), filtered, and the filtrate concentrated under reduced pressure. The residue was purified by flash chromatography (60% ethyl acetate in hexanes) to provide the title compound. $^1$H NMR (300 MHz, CDCl$_3$) δ 7.96 (d, 2H), 7.85 (m, 3H), 7.57 (m, 3H), 7.41 (d, 2H), 7.22 (d, 1H), 3.02 (s, 3H), 1.33 (s, 9H); MS (m/z) 398.

EXAMPLE 37

N-(4-tert-butylphenyl)-4-[5-(trifluoromethyl)-1H-pyrazol-1-yl]benzamide

Example 37A

4-[5-(trifluoromethyl)-1H-pyrazol-1-yl]benzoic Acid

A mixture of 4-hydrazinobenzoic acid (0.501 g, 3.29 mmol) and 4ethoxy-1,1,1-trifluoro-3-buten-2-one (0.48 mL, 3.4 mmol) in EtOH (15 mL) was heated to 75° C. for 17 hours, allowed to cool to room temperature, and concentrated under reduced pressure to provide a solid. The obtained solid was suspended in CHCl$_3$ (15 mL), treated with P$_2$O$_5$ (0.50 g, 3.5 mmol), and heated at 65° C. for 6 hours. After cooling to room temperature, the mixture was treated with 1N NaOH (5 mL) and stirred for 30 minutes. The mixture was quenched with 1N HCl (6 mL) and extracted with CH$_2$Cl$_2$ (3×8 mL). The extracts were combined, dried (Na$_2$SO$_4$), filtered, and the filtrate concentrated to provide the title compound as a solid.

EXAMPLE 37B

N-(4-tert-butylphenyl)-4-[5-(trifluoromethyl)-1H-pyrazol-1-yl]benzamide

The product from Example 37A (37.3 mg, 0.146 mmol), 4tert-butylaniline (28 µL, 0.18 mmol), PS-DCC (1.27 mmol/g, 0.342 g, 0.435 mmol), HOBT (20.2 mg, 0.149mmol), and triethylamine (0.062 mL, 0.45 mmol) in DMF (1.5 mL) were combined and heated at 65° C. for 16 hours. The mixture was allowed to cool to room temperature, filtered, and the filtrate was diluted with diethyl ether (20 mL). The diethyl ether was washed with water (10 mL), brine (10 mL), dried (Na$_2$SO$_4$), filtered, and the filtrate concentrated under reduced pressure. The residue was purified by flash chromatography (15% ethyl acetate in hexanes) to provide the title compound as a solid. $^1$H NMR (300 MHz, CDCl$_3$) δ 7.99 (d, 2H), 7.83 (br s, 1H), 7.76 (m, 1H), 7.63 (d, 2H), 7.52 (d, 2H), 7.41 (d, 2H), 6.87 (m, 1H), 1.33 (s, 9H); MS (m/z) 388.

EXAMPLE 38

N-[4-(1-azepanyl)phenyl]-4-[5-(trifluoromethyl)-1H-pyrazol-1-yl]benzamide

The title compound was prepared using the procedure in Example 37B replacing 4-tert-butylaniline with 4-(1-azepanyl)aniline. $^1$H NMR (300 MHz, CDCl$_3$) δ 7.98 (d, 2H), 7.75 (s, 1H), 7.69 (br s, 1H), 7.62 (d, 2H), 7.43 (d, 2H), 6.86 (s, 1H), 6.69 (d, 2H), 3.47 (t, 4H), 1.79 (m, 4H), 1.55 (m, 4H); MS (m/z) 429.

EXAMPLE 39

N-[4-(trifluoromethyl)phenyl]-4-[5-(trifluoromethyl)-1H-pyrazol-1-yl]benzamide

The product from Example 37A (69.8 mg, 0.272 mmol) and DMF (1 drop) in CH$_2$Cl$_2$ (2 mL) was treated with (COCl)$_2$ (29 mL, 0.33 mmol). After stirring for 5 hours, the mixture was concentrated and the residue dissolved in CH$_2$Cl$_2$ (2 mL). The mixture was treated with DMAP (35.8 mg, 0.29 mmol), pyridine (22 mL, 0.27 mmol), and 4-trifluoromethylaniline (41 mL, 0.33 mmol). The mixture was heated at 60° C. for 15 hours, allowed to cool to room temperature, diluted with 1N HCl (4 mL), extracted with $CH_2Cl_2$ (2×4 mL), dried ($Na_2SO_4$), filtered, and the filtrate concentrated under reduced pressure. The residue was purified by flash chromatography (15% ethyl acetate in hexanes) to provide the title compound as a solid. $^1$H NMR (300 MHz, $CDCl_3$) δ 8.02 (d, 2H), 7.93 (br s, 1H), 7.80 (d, 2H), 7.77 (m, 1H), 7.68 (d, 2H), 7.66(d, 2H), 6.88 (m, 1H); MS (m/z) 400, 417.

EXAMPLE 40

4-[5-(trifluoromethyl)-1H-pyrazol-1-yl]-N-[5-(trifluoromethyl)-2-pyridinyl]benzamide The title compound was prepared using the procedure in Example 39 replacing 4-trifluoromethylaniline with 5-(trifluoromethyl)-2-pyridinamine. $^1$H NMR (300 MHz, $CDCl_3$) δ 8.74.(br s, 1H), 8.60 (m, 1H), 8.54 (d, 1H), 8.08 (d, 2H), 8.01 (dd, 1H), 7.77 (m, 1H), 7.70 (d, 2H), 6.88 (d, 1H); MS (m/z) 401.

EXAMPLE 41

4-tert-butyl-N-[4-(3-chloro-2-pyridinyl)phenyl]benzamide

EXAMPLE 41A 4-(3-chloro-2-pyridinyl)aniline

The product from Example 24A (104 mg, 0.444 mmol) and triethylamine (0.095 mL, 0.68 mmol) were combined in DMF (3 mL) and treated with diphenylphosphoryl azide (0.14 mL, 0.65 mmol). After stirring for 4 hours, the mixture was treated with water (0.30 mL) and heated at 65° C. for 1 hour. The mixture was allowed to cool to room temperature, diluted with water (7 mL), and extracted with diethyl ether (7 mL). The organic layer was washed with brine (7 mL), dried ($Na_2SO_4$), filtered, and the filtrate concentrated under reduced pressure. The residue was purified by flash chromatography (50% ethyl acetate in hexanes) to provide the title compound.

EXAMPLE 41B 4-tert-butyl-N-[4-(3-chloro-2-pyridinyl)phenyl]benzamide

The product from Example 41A (17.5 mg, 0.0855 mmol), DMAP (catalytic amount), and pyridine (21 µL, 0.26 mmol) were combined in $CH_2Cl_2$ (0.5 mL) and treated with 4-tert-butylbenzoyl chloride (33 µL, 0.17 mmol). After stirring for 1 hour, the mixture was diluted with saturated $NaHCO_3$ (1 mL) and extracted with $CH_2Cl_2$ (3×1 mL). The organic layer was dried ($Na_2SO_4$), filtered, and the filtrate concentrated under reduced pressure. The residue was purified by flash chromatography (50% diethyl ether in hexanes) to provide the title compound. $^1$H NMR (300 MHz, $CDCl_3$)δ 8.59 (dd, 1H), 7.91 (br s, 1H), 7.83 (d, 2H), 7.81 (dd, 1H), 7.78 (d, 4H), 7.51 (d, 2H), 7.21 (dd, 1H), 1.36 (s, 9H); MS (m/z) 365.

EXAMPLE 42

N-(4-tert-butylphenyl)-4-(3-isoxazolyl)benzamide

EXAMPLE 42A 4-bromobenzaldehyde Oxime

A mixture of 4-bromobenzaldehyde (1.00 g, 5.40 mmol) and hydroxylamime hydrochloride (0.455 g, 6.55 mmol) were combined in EtOH (15 mL) and heated at 70° C. for 20 hours. The mixture was allowed to cool to room temperature, concentrated under reduced pressure, and diluted with ethyl acetate (40 mL). The ethyl acetate was washed with saturated $NaHCO_3$ (15 mL), dried ($Na_2SO_4$), filtered, and the filtrate concentrated under reduced pressure to provide the title compound which was used in the next step without further purification (0.906 g, 4.53 mmol, 84%).

EXAMPLE 42B 3-(4-bromophenyl)-5-(trimethylsilyl)isoxazole

The product from Example 42A (0.124 g, 0.621 mmol) and trimethylsilylacetylene (0.35 mL, 2.5 mmol) were combined in tetrahydrofuran (2.2 mL), treated bleach (2.2 mL), and stirred for 22 hours. The mixture was diluted with ethyl acetate (7 mL), washed with brine (5 mL), dried ($Na_2SO_4$), filtered, and the filtrate concentrated under reduced pressure. The residue was purified by flash chromatography (7% ethyl acetate in hexanes) to provide the title compound.

EXAMPLE 42C 3-(4-bromophenyl)isoxazole

The product from Example 42B (0.103 g) in EtOH (0.7 mL) and MeCN (2.1 mL) was treated with CsF (72 mg, 0.47 mmol), stirred for 5 minutes, diluted with saturated $NH_4Cl$ (7 mL), and extracted with $CH_2Cl_2$ (2×7 mL). The organic extract was dried ($Na_2SO_4$), filtered, and the filtrate concentrated under reduced pressure. The residue was purified by flash chromatography (7% ethyl acetate in hexanes) to provide the title compound.

EXAMPLE 42D

N-(4-tert-butylphenyl)-4-(3-isoxazolyl)benzamide

The product from Example 42C (56.1 mg, 0.250 mmol), triethylamine (55 µL, 0.39 mmol), 4-tert-butylaniline (52 µL, 0.33 mmol), and Pd(dppf)$Cl_2$:$CH_2Cl_2$ (20.4 mg, 0.025 mmol) were combined in tetrahydrofuran (10 mL) and heated at 120° C. under a carbon monoxide atmosphere (700 psi) for 16 hours. The mixture was allowed to cool to room temperature and concentrated under reduced pressure. The residue was purified by flash chromatography (20% ethyl acetate in hexanes) to provide the title compound as a solid. $^1$H NMR (300 MHz, $CDCl_3$)δ 8.51 (d, 1H), 7.96 (s, 4H), 7.82 (br s, 1H), 7.57 (d, 2H), 7.41 (d, 2H), 6.73 (d, 1H), 1.33 (s, 9H); MS (m/z) 321.

EXAMPLE 43

N-(4-tert-butylphenyl)-4-(3-fluoro-2-pyridinyl)benzamide

The product from Example 3 (52.0 mg, 0.145 mmol) in 48% $HBF_4$ (0.75 mL) and water (0.1 mL) was treated with solid $NaNO_2$ (11.9 mg, 0.172 mmol) at 0° C. After stirring for 30 minutes, the layers were allowed to separate and the liquid was layer was removed by pipette. The remaining solid was dried under reduced pressure and slurried in toluene (1.5 mL). The suspension was heated at 100° C. for 2.5 hours, allowed to cool to room temperature, and the toluene was removed by pipette. The residue was treated with 1N NaOH (1 mL) and $CHCl_3$ (1 mL) and stirred for 15 minutes. The phases were allowed to separate and the aqueous layer was extracted with $CHCl_3$ (2×1 mL). The organic layers were combined, dried ($Na_2SO_4$), filtered, and the filtrate concentrated under reduced pressure. The residue was purified by flash chromatography (20% ethyl acetate in hexanes) to provide the title compound. $^1H$ NMR (300 MHz, $CDCl_3$) δ 8.56 (dt, 1H), 8.12 (d, 2H), 7.98 (d, 2H), 7.84 (br s, 1H), 7.59 (d, 2H), 7.53 (ddd, 1H), 7.40 (d, 2H), 7.33 (ddd, 1H), 1.33 (s, 9H); MS (m/z) 349.

EXAMPLE 44

N-(4-tert-butylphenyl)-4-{3-[(dimethylamino)sulfonyl]-2-pyridinyl}benzamide

EXAMPLE 44A

2-chloro-N,N-dimethyl-3-pyridinesulfonamide

2-Chloro-3-pyridinesulfonyl chloride in THF (10 mL) was treated with a 2.0M solution of dimethylamine in THF (8 mL, 16 mmol). After stirring for 10 hours, the mixture was quenched with saturated aqueous $NH_4Cl$ and extracted with ethyl acetate. The organics were concentrated under reduced pressure and the residue was purified by flash chromatography (30% ethyl acetate in hexanes) to provide the title compound.

EXAMPLE 44B

4-{3-[(dimethylamino)sulfonyl]-2-pyridinyl}benzoic Acid

The product from Example 44A (1.29 g, 5.85 mmol), 4-carboxyphenylboronic acid (0.967 g, 5.82 mmol) and $Pd(PPh_3)_4$ (0.337 g, 0.292 mmol) were combined in 1:1 0.5 M $Na_2CO_3$:MeCN (46 mL) and heated at 85° C. overnight. The mixture was allowed to cool to room temperature, filtered through celite, and the filtrate was concentrated to 50% volume. The aqueous layer was acidified with concentrated HCl and extracted with $CH_2Cl_2$. The organics were dried ($Na_2SO_4$), filtered, and the filtrate was concentrated under reduced pressure to provide the title compound as a solid.

EXAMPLE 44C

N-(4-tert-butylphenyl)-4-{3-[(dimethylamino)sulfonyl]-2-pyridinyl}benzamide

The product from Example 44B (0.917 g, 2.99 mmol) and DMF (0.03 mL) were combined in $CH_2Cl_2$ (9 mL) and treated with $(COCl)_2$ (0.32 mL, 3.7 mL). After stirring for 90 minutes, the mixture was diluted with toluene (2 mL) and concentrated to dryness. The residue was dissolved in $CH_2Cl_2$ (9 mL) and treated with pyridine (0.36 mL, 4.5 mmol), DMAP (catalytic amount), and 4-tert-butylaniline (0.57 mL, 3.6 mmol). After stirring for 1 hour, the mixture was diluted with water and extracted with $CH_2Cl_2$. The organics were dried over $Na_2SO_4$, filtered, and the filtrate was concentrated under reduced pressure. The residue was purified by flash chromatography (75% ethyl acetate in hexanes) to provide the title compound as a solid. $^1H$ NMR (300 MHz, $CDCl_3$)δ 8.84 (dd, 1H), 8.44 (dd, 1H), 7.98 (d, 2H), 7.83 (br s, 1H), 7.72 (d, 2H), 7.58 (d, 2H), 7.51 (dd, 1H), 7.41 (d, 2H), 2.43 (s, 6H), 1.33 (s, 9H); MS (m/z) 438.

EXAMPLE 45

N-[4-(1-azepanyl)phenyl]-4-{3-[(dimethylamino)sulfonyl]-2-pyridinyl}benzamide The title compound was prepared using the procedure in Example 44C replacing 4-tert-butylaniline with 4-(1-azepanyl)aniline. $^1H$ NMR (300 MHz, DMSO-$d_6$) δ 10.02 (s, 1H), 8.89 (dd, 1H), 8.35 (dd, 1H), 8.00 (d, 2H), 7.69 (dd, 1H), 7.61 (d, 2H), 7.54 (d, 2H), 3.45 (t, 4H), 2.49 (s, 6H), 1.73 (m, 4H), 1.47 (m, 4H); MS (m/z) 479.

The foregoing is merely illustrative and is not intended to limit the invention to the disclosed compounds. Variations and changes which are obvious to one skilled in the art are to be within the scope and nature of the invention which are defined in the appended claims.

What is claimed is:
1. A compound of formula (I)

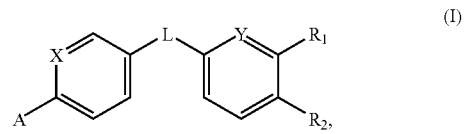

or a pharmaceutically acceptable salt, amide, ester, or prodrug thereof, wherein
  A is isoxazolyl, isothiazolyl, oxadiazolyl, oxazolyl, pyridinyl, pyridazinyl, pyrimidinyl, pyrazinyl, pyrazolyl, pyrrolyl, thiazolyl or thienyl,
  X is CH;
  Y is CH;
  L is —C(O)N($R_3$)—;
  $R_1$ is hydrogen, alkoxy, alkyl, aryloxy, haloalkoxy, haloalkyl, or halogen;
  $R_2$ is hydrogen, alkoxy, alkyl, haloalkoxy, haloalkyl, or halogen; and
  $R_3$ is hydrogen.
2. The compound according to claim 1 wherein
  A is isoxazolyl, isothiazolyl, oxadiazolyl, oxazolyl, pyridinyl, pyridazinyl, pyrimidinyl, pyrazinyl, pyrazolyl, pyrrolyl, thiazolyl or thienyl;
  X is CH;
  Y is CH; and
  L is —C(O)N($R_3$)—.
3. The compound according to claim 1 wherein
  A is imidazolyl, isoxazolyl, isothiazolyl, oxadiazolyl, oxazolyl, pyridinyl, pyridazinyl, pyrimidinyl, pyrazinyl, pyrazolyl, pyrrolyl, thiazolyl or thienyl;
  X is CH;

Y is CH;

L is —C(O)N(R₃)—; and R₁ and R₂ are independently hydrogen, alkoxy, alkyl, haloalkoxy, or haloalkyl.

4. The compound according to claim 3 that is
N-(4-tert-butylphenyl)-4-(2-pyridinyl)benzamide;
-(4-tert-butylphenyl)-4-(3-nitro-2-pyridinyl)benzamide;
4-(3-amino-2-pyridinyl)-N-(4-tert-butylphenyl)benzamide;
4-[3-(acetylamino)-2-pyridinyl]-N-(4-tert-butylphenyl)benzamide;
N-(4-tert-butylphenyl)-4-(1,3-thiazol-2-yl)benzamide;
N-(4-tert-butyl phenyl)-4-(2-pyrimidinyl)benzamide;
N-(4-tert-butylphenyl)-4-(3-cyano-2-pyridinyl)benzamide;
N-(4-tert-butylphenyl)-4-(2-thienyl)benzamide;
4-{3-[acetyl(methylsulfonyl)amino]-2-pyridinyl}-N-(4-tert-butylphenyl)benzamide;
4-(6-bromo-2-pyridinyl)-N-(4-ter-t-butylphenyl)benzamide;
ethyl 2-(4-{[(4-tert-butylphenyl)amino]carbonyl}phenyl)-3-pyridinylcarbamate;
4-(3-{bis[(chloromethyl)sulfonyl]amino}-2-pyridinyl)-N-(4-tert-butylphenyl)benzamide;
N-(4-tert-butylphenyl)-4-(2-pyridinyl)benzenesulfonamide;
N-(4-tert-butylphenyl)-4-(1H-pyrazol-1-yl)benzamide;
N-(4-tert-butylphenyl)-4-(3-pyridinyl)benzamide;
N-(4-tert-butylphenyl)-6-(1H-pyrazol-1-yl)nicotinamide;
N-(4-tert-butylphenyl)-4-(4-pyrid inyl)benzamide;
N-(4-tert-butylphenyl)-4-(1,3-oxazol-2-yl)benzamide;
N-(4-tert-butylphenyl )-4-(3-chloro-2-pyridinyl)benzamide;
4-(3-chloro-2-pyridinyl)-N-(3-methylphenyl)benzamide;
4-(3-chloro-2-pyridinyl)-N-(4-methylphenyl)benzamide;
4-(3-chloro-2-pyridinyl)-N-(4-methoxyphenyl)benzamide;
4-(3-chloro-2-pyridinyl)-N-[3-(trifluoromethoxy)phenyl]benzamide;
4-(3-chloro-2-pyridinyl)-N-(3,4-dimethylphenyl)benzamide;
4-(3-chloro-2-pyridinyl)-N-(4-ethylphenyl)benzamide;
4-(3-chloro-2-pyridinyl)-N-(4-isopropylphenyl)benzamide;
N-(4-tert-butylphenyl)-4-[5-(trifluoromethyl)-1H-pyrazol-1-yl]benzamide;
N-[4-(trifluoromethyl)phenyl]-4-[5-(trifluoromethyl)-1H-pyrazol-1-yl]benzamide;
N-(4-tert-butylphenyl)-4-(3-isoxazolyl)benzamide; or
N-(4-tert-butylphenyl)-4-(3-fluoro-2-pyridinyl)benzamide.

5. A compound that is 4-{3-[bis(methylsulfonyl)amino]-2-pyridinyl}-N-(4-tert-butylphenyl)benzamide.

6. A compound that is N-(4-tert-butylphenyl)-4-{3-[(dimethylamino)sulfonyl]-2-pyridinyl}benzamide.

7. A pharmaceutical composition comprising a therapeutically effective amount of a compound according to claim 1 or a pharmaceutically acceptable salt thereof.

\* \* \* \* \*